US00PP14880P2

(12) United States Plant Patent
Cain et al.

(10) Patent No.: US PP14,880 P2
(45) Date of Patent: Jun. 8, 2004

(54) PLUM TREE NAMED 'SUPLUMTWENTYNINE'

(50) Latin Name: *Prunus salicina*
Varietal Denomination: Suplumtwentynine

(75) Inventors: David W. Cain, Bakersfield, CA (US); Terry A. Bacon, Bakersfield, CA (US)

(73) Assignee: Sun World International, Inc., Bakersfield, CA (US)

( * ) Notice: Subject to any disclaimer, the term of this patent is extended or adjusted under 35 U.S.C. 154(b) by 0 days.

(21) Appl. No.: 10/464,235

(22) Filed: Jun. 17, 2003

(51) Int. Cl.[7] ..... A01H 5/00
(52) U.S. Cl. ..... Plt./184

(58) Field of Search ..... Plt./184

(56) References Cited

U.S. PATENT DOCUMENTS

| | | |
|---|---|---|
| PP4,902 P | 10/1982 | Weinberger |
| PP5,487 P | 6/1985 | Weinberger |
| PP7,443 P | 2/1991 | Weinberger et al. |

*Primary Examiner*—Bruce R. Campell
*Assistant Examiner*—W C Haas
(74) *Attorney, Agent, or Firm*—Knobbe, Martens, Olson & Bear LLP

(57) ABSTRACT

A new and distinct plum variety that possesses heavy and consistent production of large, firm, moderately juicy fruit with good flavor. The fruit has a smooth, black, acidic flavored skin. The flesh becomes red as the fruit matures.

1 Drawing Sheet

Latin name of the genus and species of the plant claimed: *Prunus salicina.*
Variety denomination: 'Suplumtwentynine'.

BACKGROUND AND SUMMARY OF THE INVENTION

The present invention relates to the discovery and asexual propagation of a new and distinct cultivar of Plum Tree, herein after referred to by the cultivar name 'Suplumtwentynine'. The variety originated by hybridization performed by David Cain. The new variety was first evaluated in 2000 by Terry Bacon on Sun World Experimental Ranch 75 near Wasco, Calif. in Kern County. The new variety is characterized by heavy and consistent production of large (65 mm diameter), firm fruit that ripens during the second half of June in the Bakersfield, Calif. area. Fruit of 'Suplumtwentynine' have smooth black skin and an acidic skin flavor. The flesh of 'Suplumtwentynine' becomes red as the fruit matures. The flavor of the fruit is good, having about 17° brix and a moderate amount of juice.

The parent varieties were first crossed in 1997, with the date of planting of February, 1998, and the date of first flowering being March, 2000. The new plum variety was first asexually propagated by Terry Bacon near Wasco, Kern County, Calif. in June 2000, by grafting onto Nemaguard rootstock.

The seed parent is Sun World breeding selection, '562-053' (unpatented), which was selected from a progeny of 'Santa Rosa' (unpatented) crossed with pollen from 'Suplumeighteen' (U.S. Plant Pat. No. 7,443). The new variety 'Suplumtwentynine' may be distinguished from its seed parent by ripening 7 days later and having fruit that develops red flesh as compared to yellow flesh for the seed parent.

The pollen parent is Sun World breeding selection, '90P-055' (unpatented), which was selected from an open-pollinated progeny of 'Suplumfifteen' (U.S. Plant Pat. No. 5,487). The new variety 'Suplumtwentynine' is distinguished from its pollen parent by ripening 14 days earlier and having fruit diameter that averages 65 mm as compared to the pollen parent that averages 61 mm.

The new variety 'Suplumtwentynine' most nearly resembles 'Suplumeleven' (U.S. Plant Pat. No. 4,902). It may be distinguished from 'Suplumeleven' by ripening 10 days earlier. Additionally, the new variety has acidic skin flavor while 'Suplumeleven' skin flavor is neutral. The new variety ripens with 'Black Amber' (unpatented) but has larger fruit (65 mm compared to 61 mm diameter with 'Black Amber') and develops red flesh while 'Black Amber' has amber-colored flesh.

The new plum tree variety cv. 'Suplumtwentynine' has been shown to maintain its distinguishing characteristics.

BRIEF DESCRIPTION OF THE FIGURE

The accompanying color photographic illustration in FIG. 1 shows typical specimens of the foliage and fruit of the present new plum variety. The illustration shows the upper and lower surface of the leaves, an exterior and sectional view of a fruit divided across its suture plane to show flesh color, pit cavity and the stone remaining in place. The photographic illustration was taken shortly after being picked (shipping ripe) and the colors are as nearly true as is reasonably possible in a color representation of this type.

DETAILED BOTANICAL DESCRIPTION OF THE INVENTION

Figure 1:
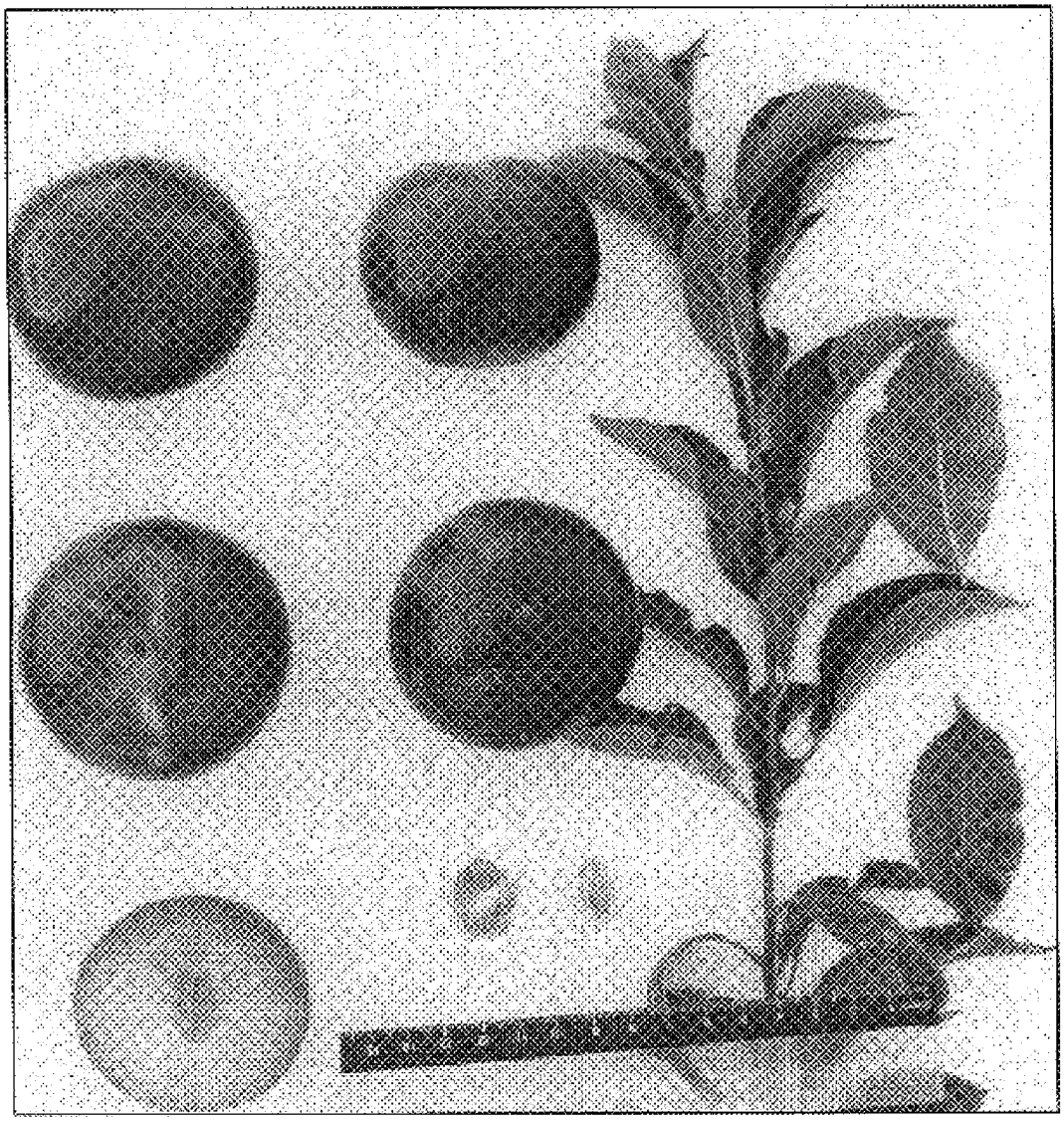

Throughout this specification, color names beginning with a small letter signify that the name of that color, as used in common speech, is aptly descriptive. Color names beginning with a capital letter designate values based upon The R.H.S. Colour Chart, published by The Royal Horticultural Society, London, England.

The descriptive matter which follows pertains to 3 year old trees grown in the vicinity of Wasco, Kern County, Calif., during 2002, and is believed to apply to plants of the variety grown under similar conditions of soil and climate elsewhere.

TREE (Measurements Taken on a 3 Year Old Tree)

General:
- *Size.*—Medium. Normal for most plum varieties. Reaches a height of approximately 3–4 meters including normal pruning.
- *Vigor.*—Vigorous; Growth of approximately 1.8 to 2 meters height the first growing season.
- *Growth.*—Upright-spreading.
- *Productivity.*—Productive. Fruit set is usually two or more times desired amount for marketable size fruit. Thinning and spacing of fruit is necessary.
- *Form.*—Vase formed.
- *Fruit bearing.*—Regular. No alternate bearing observed.
- *Fertility.*—Somewhat self-fertile but pollinizer improves fruit set.
- *Density of foliage.*—Dense. Pruning is required to open tree vase shape, allowing more sunlight to center of tree.
- *Hardiness.*—Hardy in all fruit growing areas of California.
- *Winter chilling requirement.*—Approximately 600 hours at or below about 7.2° C.
- *Tree resistance/susceptibility.*—No specific testing for relative plant disease resistance/susceptibility has been designed. Under close observation in Kern County, Calif., no particular plant/fruit disease resistance/susceptibility has been observed.
- *Root stock.*—Nemaguard.

Trunk: (Measurements at 30 cm above soil line)
- *Diameter.*—Approximately 9 cm; Varies with soil type, fertility, climatic conditions and cultural practices.
- *Surface texture.*—Medium shaggy, increases with age of tree.
- *Color.*—Varies from about Greyed-orange 164B in recesses of the bark, to about Grey 201A on the surface of the bark. Becomes darker with age.

Branches: (Measurements at 90 cm above soil line)
- *Diameter.*—Approximately 4 to 5 cm.
- *Surface texture.*—Smooth on 1st year wood, increasing roughness with tree age.
- *Color.*—Branches vary from about Greyed-orange 164B in recesses of the bark, to Grey 201A on the surface of the bark.

Branch lenticels:
- *Number.*—Numerous.
- *Length.*—Approximately 4 mm.
- *Width.*—Approximately 2 mm.
- *Color.*—About Grey-Brown 199D.

LEAVES (Data Taken in July on Fully Expanded Leaf at Midpoint of Current-Season Growth)

General:
- *Average length.*—Approximately 70 mm.
- *Average width.*—Approximately 33 mm.
- *Form.*—Broadly elliptic.
- *Leaf blade tip.*—Cuspidate.
- *Leaf base.*—Oblique.
- *Margin.*—Finely crenate.
- *Venation.*—Pinnately net veined.
- *Thickness.*—Medium.
- *Color of upper surface.*—About Green 137A.
- *Color of lower surface.*—About Green 138B.
- *Surface texture.*—Smooth.

Petiole:
- *Length.*—Approximately 8 mm.
- *Diameter.*—Approximately 2 mm.
- *Color.*—About Green 138C.

Glands:
- *Average number.*—Varies from approximately 0 to 4.
- *Positioning.*—Alternate on base of leaf blade.
- *Size.*—Approximately 0.5 mm by 0.5 mm.
- *Shape.*—Globose.
- *Color.*—About Greyed-purple 185A.

Stipules:
- *Number of stipules per bud.*—Approximately 2.
- *Length.*—Approximately 3 to 5 mm.

FLOWERING SHOOTS (Data Taken in July at Midpoint of Current-Season Growth)

- *Diameter.*—Approximately 5 mm.
- *Color.*—About Greyed-orange 165B, with slightly green background color.

Flowering shoot leaf buds:
- *Shape.*—Ovoid.
- *Length.*—Approximately 1 mm.
- *Width.*—Approximately 0.7 mm.
- *Color.*—About Greyed-orange 166B.

Flowering shoot flower buds:
- *Number per node.*—Approximately 2 to 4.
- *Shape.*—Ovoid.
- *Length.*—Approximately 2 mm.
- *Width.*—Approximately 1 mm.
- *Color.*—About Greyed-orange 166B.

FLOWERS

General:
- *Date of first bloom.*—Feb. 28, 2002.
- *Date of full bloom.*—Mar. 3, 2002.
- *Size (diameter of the fully open flower).*—Approximately 22 mm.
- *Flower aroma.*—Very slight.

Peduncle:
- *Length.*—Approximately 8 mm.
- *Diameter.*—Approximately 1 mm.
- *Color.*—About Yellow-green 149A.

Petals:
- *Number per flower.*—5.
- *Arrangement.*—Overlapping.
- *Length.*—Approximately 9 mm.
- *Width.*—Approximately 7 mm.
- *Shape.*—Elliptic.
- *Apex shape.*—Rounded.
- *Base shape.*—Narrows at point of attachment.
- *Color (fully opened flower).*—White.
- *Surface texture.*—Smooth.
- *Margins.*—Smooth.

Sepals:
- *Number per flower.*—5.
- *Length.*—Approximately 3.5 mm.

*Width.*—Approximately 2.5 mm.
*Shape.*—Obovate.
*Color.*—About Yellow-green 149A.
*Surface texture.*—Smooth.

Stamens:
*Number per flower.*—Approximately 22 to 25 (average 23).
*Length.*—Approximately 7 mm.
*Filament color.*—White.
*Anther color* (*just before dehiscence*).—About Yellow-orange 18A with highlights of about Orange-red 33B.
*Pollen color.*—About Greyed-orange 168A.

Pistil:
*Number of pistils per typical flower.*—Usually one.
*Frequency of supplementary pistils.*—Occasionally two.
*Pistil Length.*—Approximately 9 mm.
*Pubescence.*—None.
*Ovary diameter.*—Approximately 1 mm.
*Stigma position in relation to anthers.*—Stigma extends below anthers.

FRUIT (Data Taken at Firm-Ripe Stage on Mature Tree Managed to Obtain Maximum Quality Under Conditions Stated Above)

General:
*Harvest date of first pick.*—Jun. 25, 2002.
*Harvest date of last pick.*—Jul. 5, 2002.
*Length* (*stem end to apex*).—Approximately 61 mm.
*Diameter in line with suture plane*—Approximately 65 mm.
*Diameter perpendicular to suture plane.*—Approximately 65 mm.
*Average weight.*—Approximately 140 gm.
*Shape viewed from apex.*—Nearly rounded, symmetrical.
*Shape viewed from side, facing suture.*—Nearly rounded, symmetrical.
*Shape viewed from side, perpendicular to suture.*—Nearly rounded, symmetrical.
*Fruit apex shape.*—Rounded, to slightly flattened.
*Fruit stem-end cavity depth.*—Shallow.

Stem:
*Length.*—Approximately 9 mm.
*Diameter.*—Approximately 2 mm.
*Color.*—About Green 143C.

Skin:
*Thickness.*—Medium.
*Adherence to flesh.*—Tenacious.
*Surface texture.*—Smooth.
*Pubescence.*—None.
*Bloom.*—Moderate.
*Ground color.*—When visible, about Yellow-green 145A.
*Overcolor.*—About Greyed-purple 187A, becoming nearly black as fruit ripens.
*Taste.*—Acidic.

Flesh:
*Color.*—Pink; about Red 36B, becoming about Red 44C as fruit matures.
*Texture.*—Fine textured and firm.
*Ripens.*—Evenly.
*Fibers.*—Few.
*Flavor.*—Mildly sweet.
*Aroma.*—Slight.
*Brix.*—Approximately 17 degrees.
*Juice.*—Moderate.
*Use.*—Dessert. Market, local and long distance.
*Keeping and shipping quality.*—Good. Holds well in cold storage for approximately 6 weeks and maintains good firmness and eating quality. Minimal bruising and scarring in packing and shipping trials.

STONE (Measurements Taken on Dried Stones)

General:
*Adherence to flesh.*—Clingstone.
*Length.*—Approximately 22 mm.
*Diameter in line with suture plane.*—Approximately 19 mm.
*Diameter perpendicular to suture plane.*—Approximately 9 mm.
*Form* (*viewed from broad side*).—Broad obovate.
*Form* (*viewed from stem end*).—Flattened, oval.
*Base shape.*—Flattened, retuse at stem attachment.
*Apex shape.*—Mucronate with a small sharp point.
*Stone surface.*—Irregularly furrowed throughout. Heavily ridged toward base. Heavily pitted throughout.
*Comparison of stone halves.*—Nearly equal.
*Ridges.*—One on each side of the suture, beginning at the base and extending throughout the length of the stone.
*Stone outgrowing keel.*—Well developed.
*Tendency to split.*—None.
*Stone color when dried.*—About Greyed-yellow 161B.

What is claimed is:

1. A new and distinct plum tree named 'Suplumtwenty-nine' as herein described and illustrated.

* * * * *